United States Patent
Bennett

(10) Patent No.: US 7,118,768 B2
(45) Date of Patent: Oct. 10, 2006

(54) MEDICAMENTS FOR TREATING COLICS

(75) Inventor: Basil Bennett, Gauteng (ZA)

(73) Assignee: Bennetts the Chemists (Proprietary) Limited, Wendywood (ZA)

(*) Notice: Subject to any disclaimer, the term of this patent is extended or adjusted under 35 U.S.C. 154(b) by 133 days.

(21) Appl. No.: 10/296,112

(22) PCT Filed: May 22, 2001

(86) PCT No.: PCT/ZA01/00063

§ 371 (c)(1),
(2), (4) Date: Nov. 22, 2002

(87) PCT Pub. No.: WO01/89506

PCT Pub. Date: Nov. 29, 2001

(65) Prior Publication Data

US 2003/0133998 A1    Jul. 17, 2003

(30) Foreign Application Priority Data

May 22, 2000    (ZA) ................... 2000/2508

(51) Int. Cl.
*A01N 65/00*    (2006.01)
(52) U.S. Cl. .................................... 424/725
(58) Field of Classification Search .............. 424/725
See application file for complete search history.

(56) References Cited

U.S. PATENT DOCUMENTS

| 3,457,350 | A | * | 7/1969 | Mallen ................. 514/255.01 |
| 3,914,425 | A | * | 10/1975 | Jaeger ........................ 514/282 |
| 4,011,258 | A | * | 3/1977 | Wetterlin et al. ........... 560/142 |
| 5,099,861 | A | * | 3/1992 | Clearman et al. ........... 131/194 |
| 5,700,789 | A | * | 12/1997 | Ogata et al. ................ 514/100 |
| 5,981,530 | A | * | 11/1999 | Ogata et al. .......... 514/254.09 |

FOREIGN PATENT DOCUMENTS

| JP | 60008227 | * | 1/1985 |
| JP | 62209023 | * | 9/1987 |
| JP | 07188002 | * | 7/1995 |
| RO | 81648 | * | 5/1983 |

* cited by examiner

Primary Examiner—Michael Meller
(74) Attorney, Agent, or Firm—D. Peter Hochberg; Sean Mellino

(57) ABSTRACT

A medicament for use in treating babies suffering from colic. The medicament comprises diphenhydramine hydrocloride (HCl), belladonna tincture, a buffer, flavorants, such as sweetener and absolute alcohol. The medicament is treated by gamma ray bombardment or having a preservative incorporated therein for increasing the medicament's shelft life. The medicament is preferably orally fed to an infant in a dose of 1 ml per kilogram of the infant's body mass, a maximum dose being 8 ml, and at about four times per hour.

28 Claims, No Drawings

MEDICAMENTS FOR TREATING COLICS

FIELD OF THE INVENTION

This invention relates to medicaments. More particularly, the present invention relates to the treatment of colics in infants.

DESCRIPTION OF THE PRIOR ART

The invention is concerned with medicaments for use in treating babies and in particular to treating babies suffering from colic. Colic is a very widespread illness suffered by babies usually under three to four months of age. Infantile colic is a syndrome characterised by paroxysmal, excessive, and inconsolable crying without identifiable cause in a healthy infant. It is also called persistent crying in infancy and 3-month colic. The behaviour of colicky infants is a cause of anxiety and worry to their parents. Many medicaments for treating this source of discomfort in babies have been proposed but none, to our knowledge is wholly satisfactory.

SUMMARY OF THE INVENTION

According to one aspect of the invention there is provided a medicament for treating colic comprising diphenhydramine HCl, belladonna tincture, a buffer and flavourants as well as absolute alcohol and has been treated to increase shelf life, wherein the alcohol constituent comprises between 2.8% and 3.2%, and preferably 3.2% by volume of the medicament. Where the alcohol is a dilute form of alcohol e.g. alcohol BP 96.4% the amount of that dilute alcohol may be increased so that the actual alcohol content is as mentioned. Conveniently the buffer is citric acid.

paraben conveniently comprises between 5 to 10 gm and preferably 10 gm per 100 l medicament.

The flavourant is preferably a sweetener. The sweetener may be a cyclamate or saccharine. Preferably however it comprises a berry, preferably raspberry, flavourant which conveniently comprises of the order of 50 ml per 100 l medicament. The sweetener may further or alternatively include syrup simplex which may conveniently comprise between 20 to 35 l and preferably 35 l per 100 l medicament.

The aqueous chloroform concentrate also serves as a preservative.

It will also be understood that the assqeous chloroform concentrate and belladonna tincture contain alcohol. The total amount of alcohol in the medicament is conveniently between 4.75% to 5.1% preferably about 5.1%. Accordingly another aspect of the invention provides a medicament for treating colic comprising diphenhydramine HCl, belladonna tincture, a buffer and flavourants and aqueous chloroform concentrate as well as absolute alcohol and has been treated to increase shelf life, wherein the alcohol content of the medicament comprises between 4.75% and 5.1%, and preferably 5.1% by volume of the medicament.

According to a further aspect of the invention there is provided a method of treating a colicky infant comprises feeding the infant a medicament as mentioned in any one of the preceding claims. The medicament is preferably administered to the infant in an amount of the of 1 ml per kilogram body mass with feeds normally four hourly with a maximum of 8 ml per dose.

An example of the medicament is given below, with the amounts set forth both for a single dosage amount and for the amounts for making 100 l. The names of the suppliers is given for identification purposes only. The ingredients may be supplied by others.

| Constituent | Purpose | Supplier | Per 5 ml | Per 100 l |
|---|---|---|---|---|
| Diphenhydramine HCl | Active | Sweizerhall | 3.125 mg | 62.5 g |
| Belladonna Tincture | Active | William Ransome | 0.125 ml | 2.5 l |
| Absolute alcohol 99% | Solvent | Illovo | 0.16 ml | 3.2 l |
| Citric acid monohydrate | Buffer | Medicolab | 6.25 mg | 125 g |
| aqueous chloroform concentrate | Flavourant | Medicolab | 0.025 ml | 0.5 l |
| methyl paraben | Preservative | Ethnichem | 5 mg | 100 g |
| propyl paraben | Preservative | Protameen Chem | 0.5 mg | 10 g |
| syrup simplex | Sweetener | Bush Boake Allen | 1.75 ml | 35 l |
| Raspberry Flavour | Sweetener | Bush Boake Allen | 0.0025 mg | 0.050 l |
| Poncho 4R | Colourant | Bush Boake Allen | 0.27 mg | 5.4 g |
| Distilled Water | Solvent | Medicolab | to 5 ml | to 100 l |

DETAILED DESCRIPTION OF THE INVENTION

The medicament may be treated to increase shelf life by being bombarded by gamma rays. Alternatively and more usually the medicament is treated to increase shelf life by incorporating a preservative as a constituent. This preservative may comprise one or more of the following, viz methyl paraben, propyl paraben, aqueous chloroform, preferably in concentrate form, and alcohol and conveniently all of these ingredients. Another preservative which may be used is sodium benzoate. The alcohol in addition to being a preservative is also the solvent for the medicament. The methyl paraben conveniently comprises between 50 to 100 gm and preferably 100 gm per 100 l medicament. The propyl The total alcohol content of this example is approximately 5.1% by volume of the medicament. This is calculated as follows:

| Absolute alcohol | 0.16 ml × 99% = | 0.1584 ml |
|---|---|---|
| Aq Chlorof. Conc | 0.025 ml × (60% × 90%) = | 0.135 ml |
| Belladona Tinc | 0.125 ml × 65% = | 0.0813 ml |
| | | 0.2553 ml |

0.2553 ml/5 ml = 5.066%.

Instead of using absolute alcohol, alcohol BP 94.4% may be used in which case a slightly greater amount may be used to have the same effect as absolute alcohol.

We have found that the raspberry flavoured sweetener is most satisfactory and also provides [in addition] a pleasant fragrance to the medicament. However other flavoured sweeteners may be used such as strawberry sweetener.

All the ingredients used are as approved by the Medical Control Council of South Africa.

In tests carried out, it was found that about 77% of the patients showed moderate or excellent improvement when treated with the above medicament. Babies had high tolerance for the medicament. Only about 11% of the babies experienced adverse events regarded as possibly related to the medicament. The most affected body system was in the digestive system where constipation was caused. In addition we have found that excess nasal mucous has in a few cases been noted. These adverse events were mild to moderate in intensity. Most of the adverse events were resolved within a short time.

Care should be exercised in using the medicament in cases where the baby suffers from epilepsy or asthma or there is a family history of these illnesses.

The medicament may be altered as will be appreciated by those skilled in the art. However the alcohol content should not be increased above that mentioned above.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall withing the spirit and scope of the appended claims.

The invention claimed is:

1. A medicament for treating colic comprising diphenhydramine HCl, belladonna tincture, a buffer and flavourants as well as absolute alcohol and has been treated to increase shelf life, wherein the alcohol concentrate comprises between 2.8% and 3.2% by volume of the medicament.

2. A medicament as claimed in claim 1 wherein the alcohol is 3.2% by volume of the medicament.

3. A medicament as claimed in claim 1 wherein the buffer is citric acid.

4. A medicament as claimed in claim 1 wherein the medicament is treated to increase shelf life by being bombarded by gamma rays.

5. A medicament as claimed in claim 1 wherein the medicament is treated to increase shelf life by incorporating a preservative as a constituent.

6. A medicament as claimed in claim 5 wherein the preservative is at least one selected from the group consisting of viz methyl paraben, propyl paraben, aqueous chloroform and alcohol.

7. A medicament as claimed in claim 6 wherein the methyl paraben is in amount of 50 to 100 gm per 100 l medicament.

8. A medicament as claimed in claim 7 wherein the methyl paraben is in an amount of 100 gm per 100 liter medicament.

9. A medicament as claimed in claim 6 wherein the propyl paraben is in an amount of 5 to 10 gm per 100 liter medicament.

10. A medicament as claimed in claim 9 wherein the propyl paraben is in an amount of 10 gm per 100l medicament.

11. A medicament as claimed in claim 1 wherein the flavourant is a sweetener.

12. A medicament as claimed in claim 11 wherein the sweetener is a berry flavourant.

13. A medicament as claimed in claim 11 wherein the sweetener includes syrup simplex.

14. A medicament as claimed in claim 13 wherein the syrup is an amount of 20 to 35 liter per 100 liter medicament.

15. A medicament as claimed in claim 14 wherein the syrup is an amount of 35 liter per 100 liter medicament.

16. A medicament for treating colic comprising diphenhydramine HCl, belladonna tincture, a buffer and flavourants and aqueous chloroform concentrate as well as absolute alcohol and has been treated to increase shelf life, wherein the alcohol content of the medicament comprises between 4.75% and 5.1% by volume of the medicament.

17. A medicament as claimed in claim 16 wherein the alcohol content of the medicament comprises 5.1% by volume of the medicament.

18. The medicament according to claim 12 wherein the berry flavourant is a raspberry flavourant.

19. The medicament according to claim 18 wherein the raspberry flavourant is an amount of 50 ml per 100 liter of medicament.

20. A medicament for a treating colic comprising diphenhydramine ACl, belladona tincture, a buffer, a flavorant, and a solvent selected from the group consisting of absolute alcohol, glycol, sorbitol and glycerine.

21. The medicament according to claim 20 wherein the medicament is treated to increase shelf life, said treatment selected from the group consisting of gamma ray bombardment and incorporating a preservative as a constituent in said medicament.

22. The medicament according to claim 21 wherein the preservative is at least one selected from the group consisting of alcohol, propylene glycol, sorbitol, glycerine, viz methyl paraben, propyl paraben, sodium benzoate an aqueous chloroform.

23. The medicament according to claim 22 wherein the alcohol is absolute alcohol.

24. The medicament according to claim 20, wherein the solvent is absolute alcohol.

25. A method of treating a colicky infant comprising the steps of:
preparing a medicament comprising:
diphenhydramine HCl;
belladona tincture;
a buffer;
a flavourant; and
absolute alcohol, wherein the alcohol is between 2.8% and 3.2% the volume of the medicament;
treating said medicament for increased shelft life; and
orally administering said medicament to the colicky infant in a dosage of 1 ml per kilogram of infant body mass.

26. A method as claimed in claim 25 wherein the medicament is supplied to the infant in an amount of 1 ml per kilogram body mass.

27. A method according to claim 25 wherein the dosage does not exceed 8 ml.

28. A method according to claim 25 wherein the dosage is administered once every four hours.

* * * * *